(12) United States Patent
Giovagnoni et al.

(10) Patent No.: US 11,357,813 B2
(45) Date of Patent: Jun. 14, 2022

(54) COMPOSITION COMPRISING TANNINS

(71) Applicant: ABOCA S.P.A SOCIETÀ AGRICOLA, Sansepolcro (IT)

(72) Inventors: Emiliano Giovagnoni, Sansepolcro (IT); Michele Burini, Sansepolcro (IT); Francesca Marini, Sansepolcro (IT)

(73) Assignee: ABOCA S.P.A. SOCIETÀ AGRICOLA, Sansepolcro (IT)

( * ) Notice: Subject to any disclaimer, the term of this patent is extended or adjusted under 35 U.S.C. 154(b) by 525 days.

(21) Appl. No.: 15/753,608

(22) PCT Filed: Aug. 19, 2016

(86) PCT No.: PCT/IB2016/054975
§ 371 (c)(1),
(2) Date: Feb. 20, 2018

(87) PCT Pub. No.: WO2017/029643
PCT Pub. Date: Feb. 23, 2017

(65) Prior Publication Data
US 2019/0125817 A1    May 2, 2019

(30) Foreign Application Priority Data
Aug. 20, 2015  (IT) .................. 102015000045541

(51) Int. Cl.
| | | |
|---|---|---|
| *A61K 36/49* | (2006.01) | |
| *A61K 36/886* | (2006.01) | |
| *A61K 36/28* | (2006.01) | |
| *A61K 36/324* | (2006.01) | |
| *A61K 36/328* | (2006.01) | |
| *A61K 36/73* | (2006.01) | |
| *A61K 36/185* | (2006.01) | |
| *A23L 33/105* | (2016.01) | |
| *A61P 17/02* | (2006.01) | |
| *A61P 29/00* | (2006.01) | |
| *A61P 1/04* | (2006.01) | |
| *A61K 9/00* | (2006.01) | |
| *A61K 36/45* | (2006.01) | |

(52) U.S. Cl.
CPC ............ *A61K 36/49* (2013.01); *A23L 33/105* (2016.08); *A61K 9/0014* (2013.01); *A61K 36/185* (2013.01); *A61K 36/28* (2013.01); *A61K 36/324* (2013.01); *A61K 36/328* (2013.01); *A61K 36/45* (2013.01); *A61K 36/73* (2013.01); *A61K 36/886* (2013.01); *A61P 1/04* (2018.01); *A61P 17/02* (2018.01); *A61P 29/00* (2018.01)

(58) Field of Classification Search
CPC ..... A23L 33/105; A61K 36/185; A61K 36/28; A61K 36/324; A61K 36/328; A61K 36/45; A61K 36/49; A61K 36/73; A61K 36/886; A61K 9/0014; A61P 17/02; A61P 1/04
See application file for complete search history.

(56) References Cited

U.S. PATENT DOCUMENTS

| | | | |
|---|---|---|---|
| 6,482,942 B1 | 11/2002 | Vittori | |
| 2010/0062087 A1* | 3/2010 | Chien | .................. A61K 31/047 424/732 |
| 2011/0223193 A1* | 9/2011 | Mercati | .................. A61P 33/00 424/195.18 |

FOREIGN PATENT DOCUMENTS

| | | | |
|---|---|---|---|
| GB | 2 48 5 483 | 5/2012 | |
| WO | 2004/096169 | 11/2004 | |
| WO | 2010/052568 | 5/2010 | |
| WO | WO-2010052568 A1 * | 5/2010 | ............... A61P 29/00 |

OTHER PUBLICATIONS

International Search Report for PCT/IB2016/054975, 6 pages, dated Nov. 21, 2016.
Written Opinion of the ISA for PCT/IB2016/054975, 7 pages, dated Nov. 27, 2017.
Al-Harbi et al. "Gastric antiulcer and cytoprotective effect of *Commiphora molmol* in rats" *Journal of Ethnopharmacology*, vol. 55, pp. 141-150 (Jan. 1997).
Gharzouli et al. "Effects of aqueous extracts from *Quercus ilex* L. root bark, *Punica granatum* L. fruit peel and *Artemisia herba-alba* Asso leaves on ethanol-induced gastric damage in rats" *Phytotherapy Research*, vol. 13, No. 1, pp. 42-45 (Feb. 1999).
Krieglstein et al. "Acetyl-11-keto-β-boswellic acid, a constituent of a herbal medicine from *Bosweliia serrata* resin, attenuated experimental ileitis" *International Journal of Colorectal Disease*, vol. 16, No. 2, pp. 88-95 (Apr. 2001).
Nosal 'Ova G. et al. "Antitussive efficacy of the complex extract and the polysaccharide of marsh mallow (*Althaea officinalis* L., var. robusta)" *Die Pharmazie, Govi Verlag Pharmazeutischer Verlag Gmbh*, vol. 47, No. 3, pp. 224-226 (Jan. 1992).
Piwowarski et al. "Anti-hyaluronidase and anti-elastase activity screening of tannin-rich plant materials used in traditional Polish medicine for external treatment of diseases with inflammatory background" *Journal of Ethnopharmacology*, vol. 137, No. 1, pp. 937-941 (May 2011).
Sutovska "Influence of Polysaccharides from *Aloe vera* (*Aloe barbadensis* Miller, *Liliaceae*) on mechanically induced cough in cats" *Acta Veterinaria Brno*, vol. 79, No. 1, pp. 51-59 (Jan. 2010).

* cited by examiner

*Primary Examiner* — Aaron J Kosar
(74) *Attorney, Agent, or Firm* — Sterne, Kessler, Goldstein & Fox P.L.L.C.

(57) ABSTRACT

The present invention relates to a novel composition capable of enhancing tannins' ability to adhere to mucous membranes (mucosas) and skin, its use as a therapeutic composition, and products consisting of or comprising said composition.

18 Claims, 6 Drawing Sheets

Hamamelis 10%

Hamamelis 5%

Hamamelis 1%

Hamamelis 0,1%

Aloe 10%

Aloe 5%

Aloe 1%

Aloe 0.1%

COMPOSITION COMPRISING TANNINS

Figure 1:
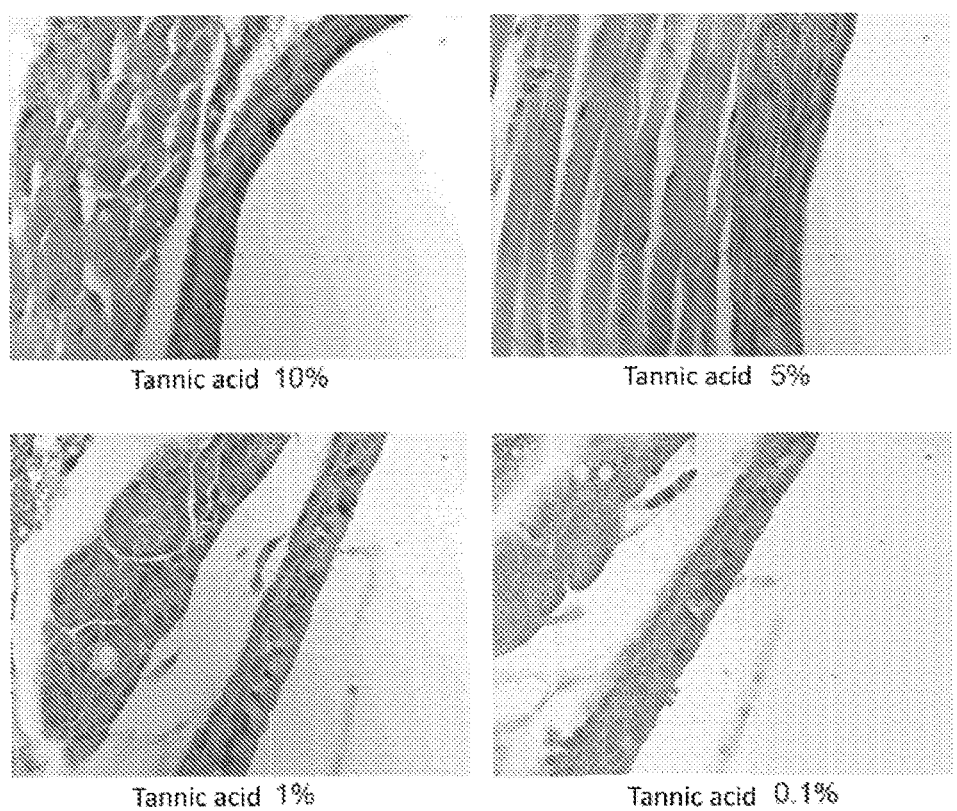

This application is the U.S. national phase of International Application No. PCT/IB2016/054975, filed Aug. 19, 2016; which designated the U.S. and claims priority to IT Patent Application No. 102015000045541, filed Aug. 20, 2015; the entire contents of each of which are hereby incorporated by reference.

The present invention relates to a novel composition capable of enhancing tannins' ability to adhere to mucous membranes (mucosas) and skin, its use as a therapeutic composition, and products consisting of or comprising said composition.

STATE OF THE PRIOR ART

Tannins are a class of substances of natural origin.

It is known in the literature that tannins provide an effective protection against pathogens (which are precipitated) and irritating substances (which are complexed), reduce secretions by the mucous membranes and reduce sensitivity of nerve terminations at the intestinal level, with an entailed reduction of peristaltic stimulation.

It is also known that tannins can form reversible complexes with proteins by hydrophobic and hydrogen bonds.

Tannins, thanks to such an ability, on the mucous surfaces they come into contact with, form an impermeable layer, below which the natural healing process is fostered; therefore, tannins assist in the healing of wounds, burnings, inflammation, and also aid to fight colonization by microorganisms.

Moreover, it is also known that tannins exert a specific anti-inflammatory and anti-diarrhoeal action: a classic example is the treatment of enteritis. Diarrhoea characterizing this disorder is originated in the large intestine, yet it responds to a stimulus coming from the small intestine, aimed at removing undesired material; i.e., it is a physiological and healthy response by the body, which can, however, lead to disastrous consequences (swift dehydration and death). In this case, tannin-based remedies are used to control the situation, yet not by 'blocking' the flow, but reducing inflammation, and therefore the triggering cause, at the small intestinal level. Though remaining a partially symptomatic approach (not necessarily removing the offending factor), it contributes at least to heal the damaged mucous membrane (mucosa) and eliminate the pathogens present. Internally, the anti-inflammatory property is used for gastritides, enteritides, esophagitides and inflammatory diseases of the intestine (ulcerous colitis, Crohn's disease).

Tannins also have a known anti-ulcer effect: in fact, they bind to proteins of lesion edges, protecting said edges from further insults.

Tannins also exert an action on microflora by reducing uremic toxin production, abating the risk of renal damage.

Moreover, they are known to have hemostatic properties, due to the combination of astringent and coagulant action; vulnerary properties, by forming a protective barrier on burnings, and are also used for the treatment of wet eczemas and viral infections.

When encountering mucous membranes, tannins induce precipitation of the proteins present, causing an increase of the barrier and protecting underlying mucosal layers from the attack of microorganisms and chemical irritants. Through this mechanism, tannins protect from pathogens and irritating substances. Tannins' actions, deriving from their non-specific complexing ability towards proteins, are several: for instance, the impervious protective layer formed by interaction with surface proteins is most likely the primary mechanism enabling a natural and quick healing in case of abrasions, burnings or inflammations.

When coming into contact with mucous membranes, tannins have as an effect the "astringency", i.e., have a superficial and local action on tissues with which they come into contact, attenuating their functional activity (secretion, absorption, excitability). Tannins do not penetrate in depth, therefore their use is limited to congestive and inflammatory states of the skin and accessible mucous membranes. As aforestated, the precipitation of the proteins present on the mucous membranes determines an increase of the barrier, protecting the underlying layers of the mucous membrane from the attack of microorganisms and chemical irritants. Tannins on mucous membranes also carry out an antisecretory action. The production of a superficial, yet temporary, protection layer makes nerve terminations less sensitive to stimulations, moreover microorganism inactivation and neutralization of inflammatory proteins is had. Tannins have a marked preference for free proteins, and for this reason they concentrate in damaged areas.

They are scarcely absorbed, and therefore perform an action at a local level. Scarce bioavailability is a factor in favour of their use, as when absorbed in high amounts they can be rather toxic. Tannins-induced injurious effects have been found mainly in all those cases in which a pathological state was had (e.g. burnings, stomach and intestine ulcers), predisposing to greater systemic absorption, which fostered their passage into blood in a high amount. In fact, some toxicity studies in which tannic acid was subcutaneously administered to laboratory animals resulted in the onset of hepatic tumours. The same ending was obtained with the subcutaneous injection of tannins deriving from tea leaves, which induced carcinomas in rodents. An epidemiological study carried out by Morton (1986) demonstrated rather aptly the connection between esophageal tumour incidence and consumption of tannins-rich foods, in certain geographical areas of the world. Bone K. and Mills S. in this regard maintain that the associations reported in the foregoing studies have scarce relevance in phytotherapy, yet in any case suggest a certain caution in the long-term use, orally of topically (damaged skin), of tannins-containing drugs.

Therefore, it is of interest to use tannins' protective ability on the one hand, reducing however their bioavailability.

SUMMARY OF THE INVENTION

The present invention relates to a novel composition capable of enhancing tannins' ability to adhere on mucous membranes and skin.

Increasing of tannins' adhesion ability enables to enhance their therapeutic effect, concomitantly reducing their bioavailability, both as tannins are retained longer on the skin or mucous membrane treated with the composition of the invention, and as the enhancement of their adhesion abilities enables to substantially decrease the dosage of tannins needed to obtain the same adhesive effect that is obtained with free tannins.

Therefore, object of the invention is a composition capable of enhancing tannins' abilities to adhere to the skin and the mucous membranes, said composition for use in a therapeutic treatment, products comprising said composition, a method for the preparing of said composition and therapeutic methods for the treatment or the protection of inflamed mucous membranes or skin and/or wounds, comprising the administration of the composition of the invention to an individual in need thereof.

Therefore, objects of the invention are: a composition comprising
from 0.05 to 1% w/w of resins,
from 0.05 to 1% w/w of tannins, and
from 0.05 to 3% w/w of polysaccharides;
its therapeutic use, product comprising it and therapeutic methods comprising the administration of said composition.

DETAILED DESCRIPTION OF THE FIGURES

FIG. 1 shows $FeCl_3$ staining of 2 μm-thick sections of white male mouse oropharynx, treated for 1 hour with 10%, 5%, 1% and 0.1% tannic acid in distilled water (weight/volume). Staining intensity is dependent on concentration.

Figure 2:
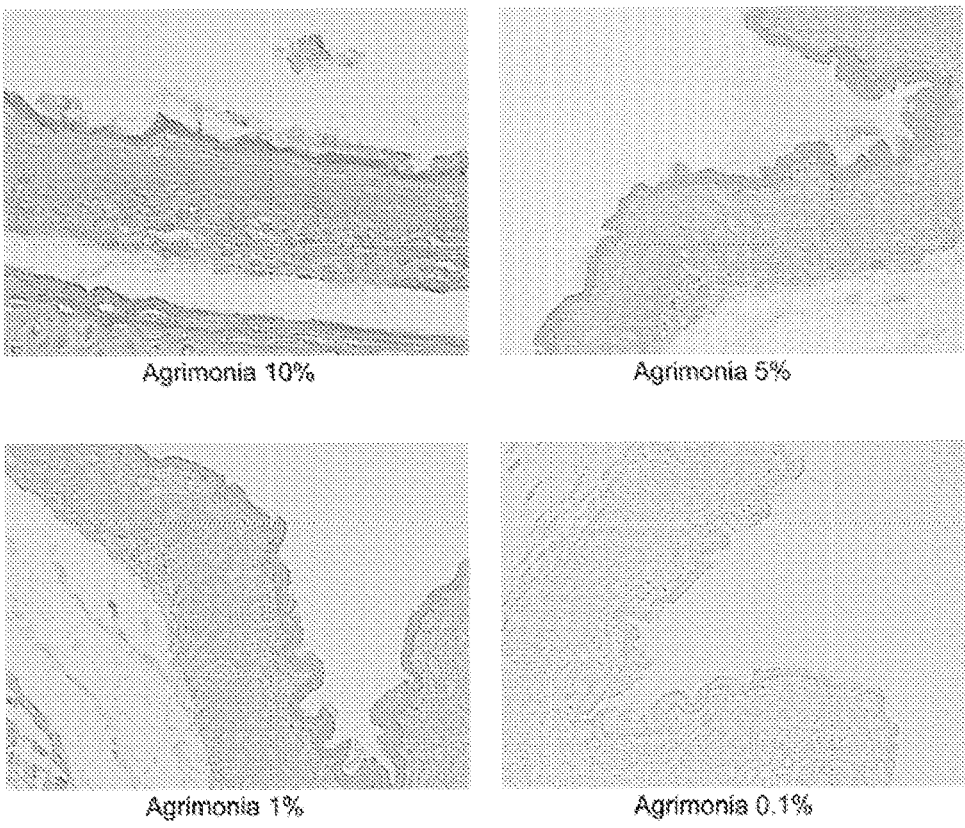

FIG. 2 shows $FeCl_3$ staining of 2 μm-thick sections of white male mouse oropharynx, treated for 1 hour with 10%, 5%, 1% and 0.1% *Agrimonia eupatoria* extract in distilled water (w/v), equal to, respectively, 100 mg/ml, 50 mg/ml, 10 mg/ml and 1 mg/ml of *Agrimonia eupatoria*. Staining intensity is dependent on concentration.

Figure 3:
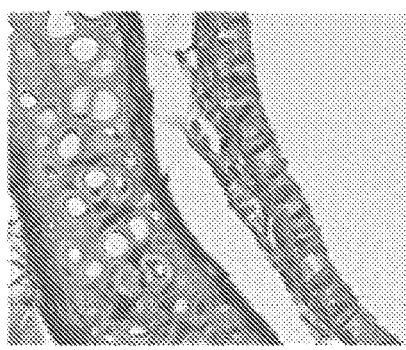
Figure 3:
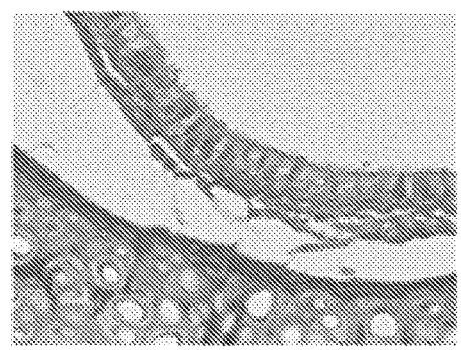
Figure 3:
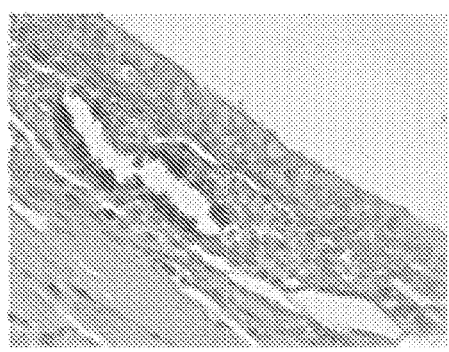
Figure 3:
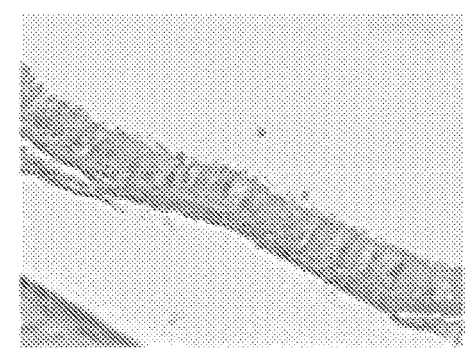

FIG. 3 shows $FeCl_3$ staining of 2 μm-thick sections of white male mouse oropharynx, treated 1 hour with 10%, 5%, 1% and 0.1% *Hamamelis Virginiana* extract in distilled water (w/v) equal to, respectively, 100 mg/ml, 50 mg/ml, 10 mg/ml and 1 mg/ml of *Hamamelis Virginiana*. Staining intensity is dependent on concentration.

Figure 4:
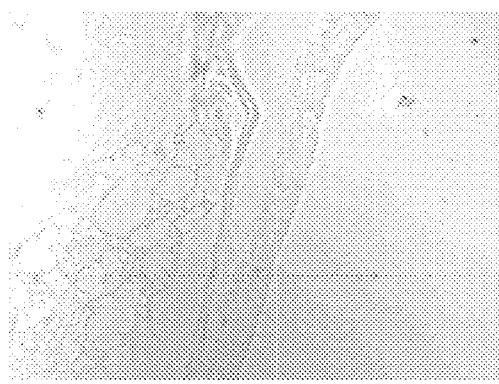
Figure 4:
Figure 4:
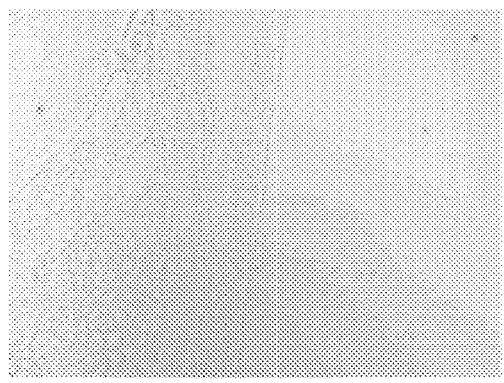
Figure 4:
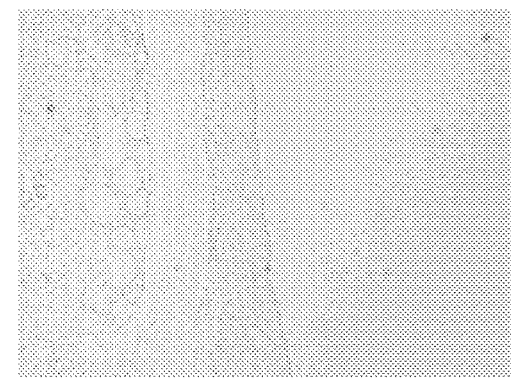

FIG. 4 shows $FeCl_3$ staining of 2 μm-thick sections of white male mouse oropharynx, treated 1 hour with 10%, 5%, 1% and 0.1% *Aloe vera* extract in distilled water (w/v). No staining is observed.

Figure 5:
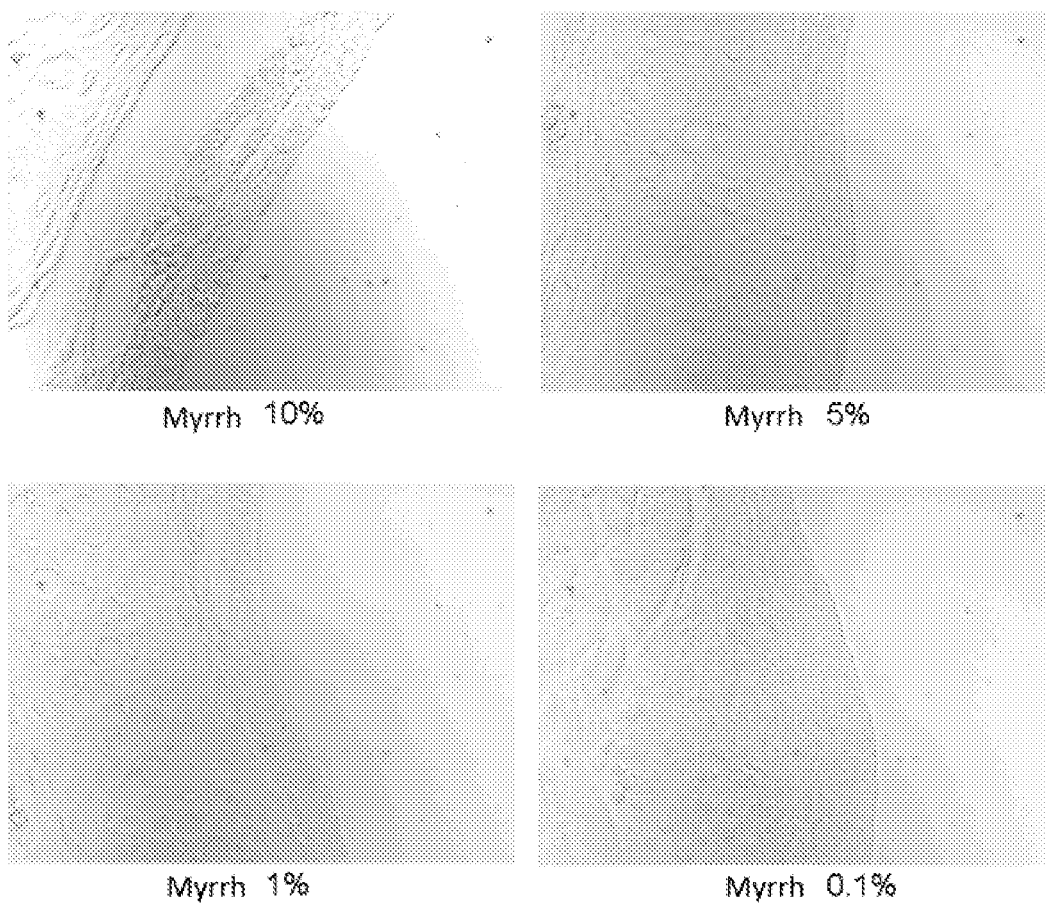

FIG. 5 shows $FeCl_3$ staining of 2 μm-thick sections of white male mouse oropharynx, treated 1 hour with 10%, 5%, 1% and 0.1% *Commiphora myrrha* vera extract in distilled water (w/v). No staining is observed.

Figure 6A:
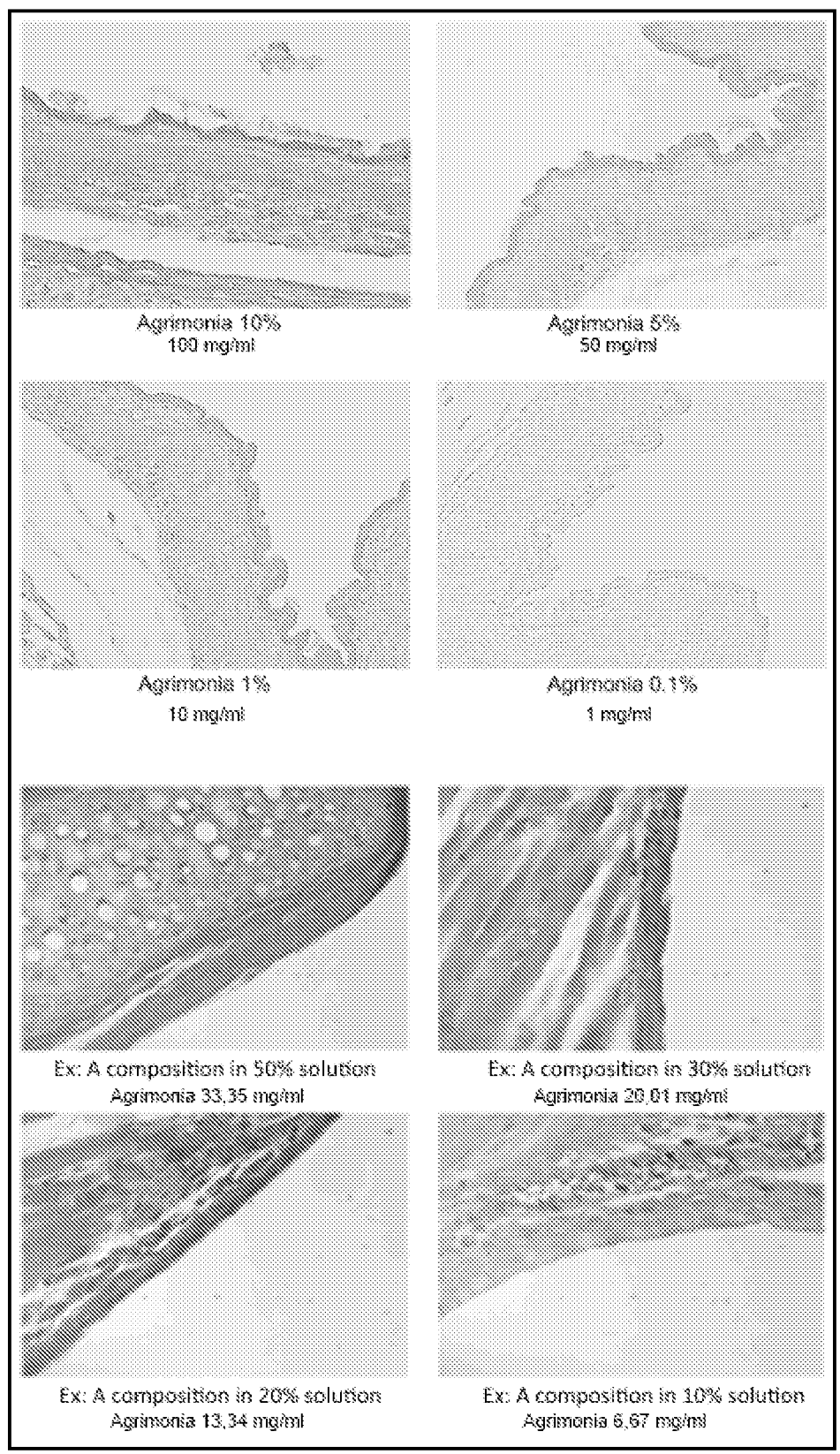
Figure 6B:
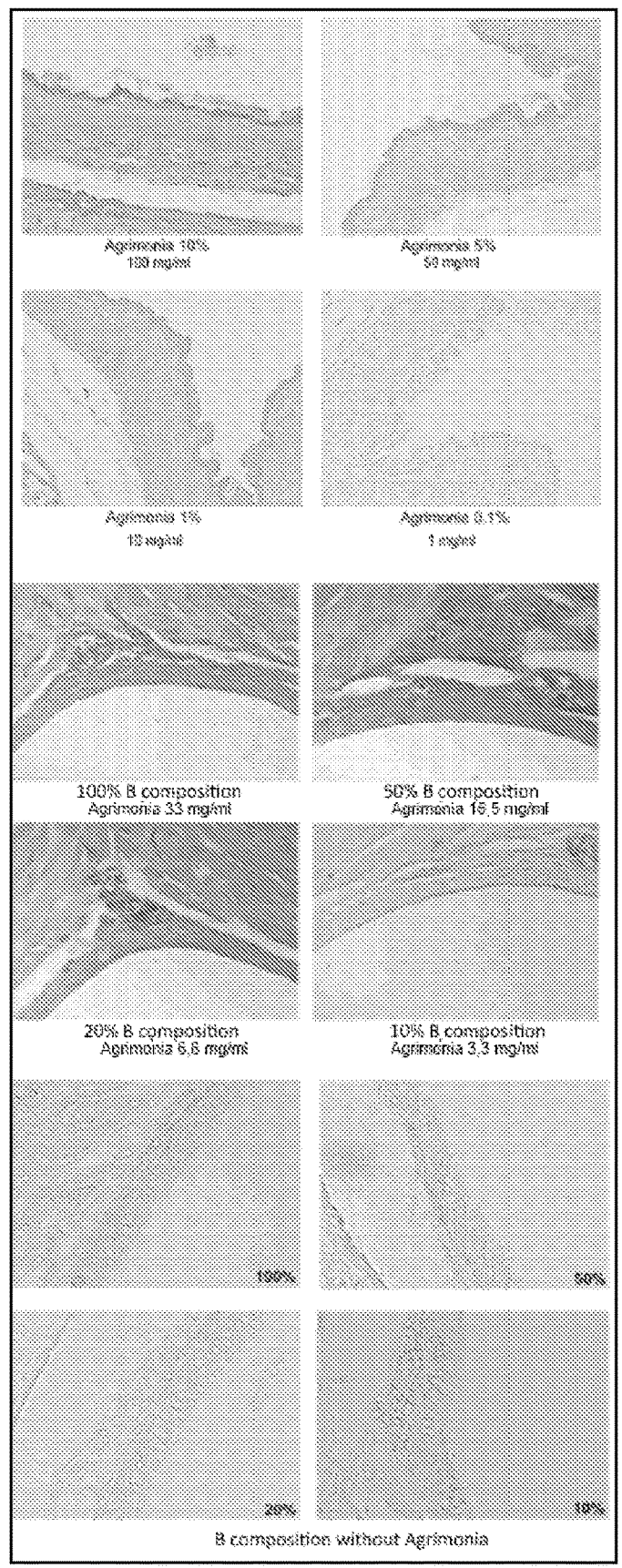
Figure 6C:
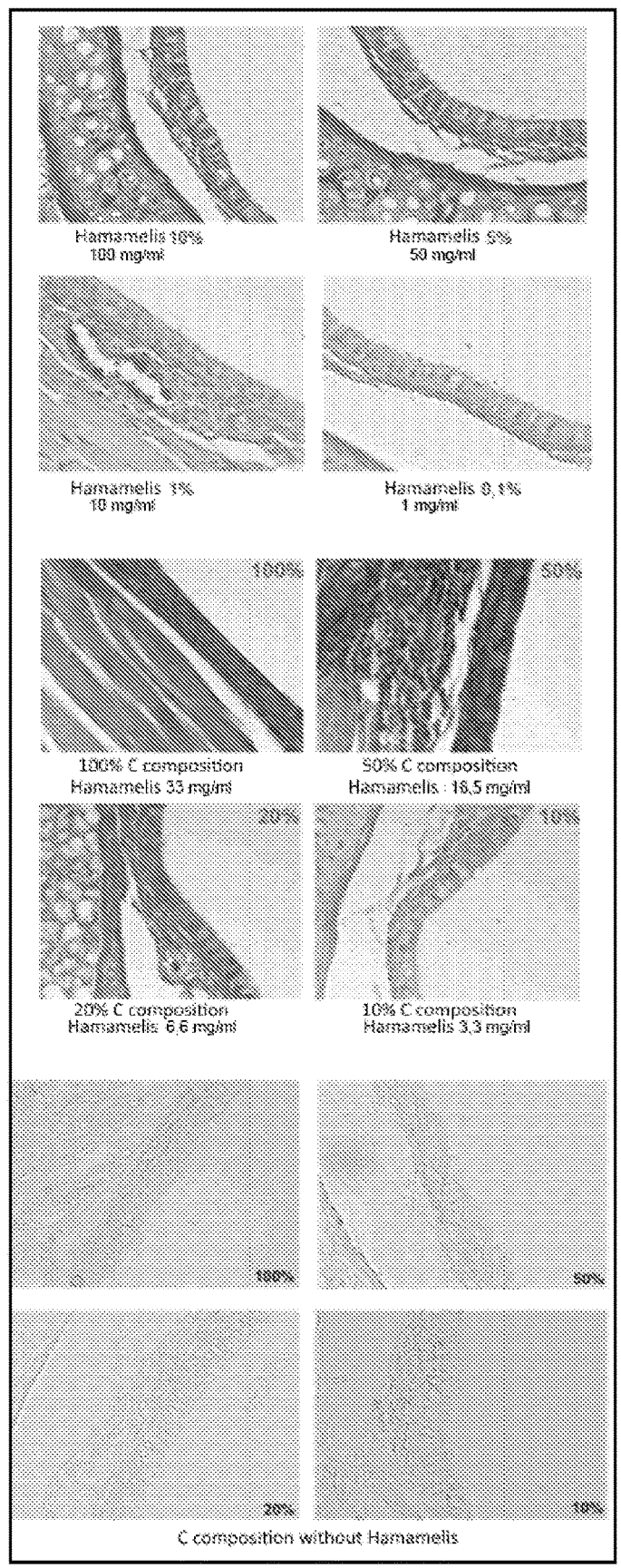

FIG. 6 shows the result of comparative examples of $FeCl_3$ staining of 2 μm-thick sections of white male mouse oropharynx, treated 1 hour with *Agrimonia eupatoria* extract and compositions of the invention containing *Agrimonia eupatoria* (panels 6a and 6b), with *Hamamelis virginiana* and composition of the invention containing *Hamamelis virginiana* (FIG. 6c). FIGS. 6b and 6c also show a control in which the mucous membrane is treated with a composition of the invention without tannins-containing extracts (*agrimonia* or *hamamelis*).

As is evident from the various panels, the presence of resins and polysaccharides increases in a clearly visible manner the ability of tannins, highlighted by the dye used, to adhere to the oral mucous membrane (mucosa).

In panel 6a it is distinctly seen how the composition of the invention has the effect of causing a staining, with only 6.7 mg/ml of *agrimonia*, equal to that obtained with an amount of from 50 and 100 mg/ml of *agrimonia*.

In panel 6b it is evident how another embodiment of the composition of the invention has the effect of causing a staining, with about 6.6 mg/ml of *agrimonia*, equal to that obtained with an amount of from 50 to 100 mg/ml of *agrimonia*, and how said composition without *agrimonia* causes no staining: therefore, the staining is actually due only to tannins present in the *agrimonia* extract, whereas staining intensity, *agrimonia* extract concentration being equal, is clearly linked to the presence of resins and polysaccharides according to the invention.

In panel 6c, finally, the effectiveness of the composition of the invention is confirmed in a further embodiment and it is evident as, in this case as well, with an amount of composition containing about 6.6 mg/ml of *hamamelis*, a staining equal to that obtained with an amount of from 50 to 100 mg/ml of *hamamelis* is obtained. It is also evident how said composition without *hamamelis* causes no staining: the staining is therefore due only to tannins present in the *hamamelis* extract, whereas staining intensity, *hamamelis* extract concentration being equal, is clearly linked to the presence of resins and polysaccharides according to the invention.

DETAILED DESCRIPTION OF THE INVENTION

In order to enhance the therapeutic and protective effectiveness of tannins, the Authors of the present invention have provided a solution in which said therapeutic effectiveness is enhanced, and preferably extended in time, substantially by enhancing tannins' ability to bind to mucous membranes and skin. Since most of the above-described therapeutic properties of tannins are carried out topically, and their effectiveness is closely dependent on tannins' ability, the Authors found a way to increase the yield of tannins' adhesion to mucous membranes and/or skin, based on the surprising discovery that the mixing of suitable amounts of tannins with suitable amounts of other components remarkably increases tannins' ability to adhere to said tissues.

The present invention provides a composition which synergistically increases tannins' ability to bind to mucous membranes or skin, thereby enabling said substances to act in a more effective, and preferably longer-lasting manner, compared to equal amounts of the same tannins outside of the composition of the invention.

In other words, the Authors of the present invention have demonstrated that the mixing of suitable amounts of tannins with suitable amounts of specific classes of components increases tannins' effectiveness of binding to mucous membranes and/or skin; as a result, in order to obtain the same amount of tannins bound to said tissues it suffices to use less tannins when these are comprised in the composition of the invention. Said mixing is also able to extend the length of time of tannins' adhesion to the abovementioned tissues, compared to that of free tannins.

Therefore, the composition of the invention is able to condensate the tannins which adhere to mucous membrane or skin when contacted with said tissues.

Therefore, to obtain the same desired effect of tannins' binding to mucous membranes a lower concentration of tannins needs to be used, thereby limiting the amount of tannins administered to the subject taking said substances.

Therefore, object of the invention is a composition comprising
from 0.05 to 1% w/w of resins,
from 0.05 to 1% w/w of tannins, and
from 0.05 to 3% w/w of polysaccharides.
In one embodiment, the composition comprises
from 0.1 to 0.7% w/w of resins,
from 0.1 to 0.8% w/w of tannins, and
from 0.1 to 1.5% w/w of polysaccharides.
According to a further embodiment, the composition comprises
from 0.1 to 0.5% w/w of resins,
from 0.2 to 0.7% w/w of tannins, and
from 0.1 to 0.8% w/w of polysaccharides.

The components of the invention can be of natural origin, synthetic, or a mixture thereof.

According to one embodiment, it is preferred a composition as described above, wherein said resins and/or wherein said tannins and/or wherein said polysaccharides are of natural origin. When the components are of natural origin, they can be extracted, e.g., at different degrees of purity from plant sources.

According to one embodiment of the invention, the components of the composition in any form described above can also be comprised in plant extracts, as long as the weight percentages of each component are in the above-indicated ranges. For this purpose, it suffices to titer the extracts into raw matters according to conventional techniques, which may be, e.g., HPLC for polysaccharides, spectrophotometry for tannins, gravimetry for resins.

The tannins according to the invention can be hydrolysable tannins, condensed tannins or a mixture thereof.

According to the present invention, in accordance with the scientific literature, by "resins of plant origin" are meant in particular oleo-gum-resins, plant exudates that can be secreted by plants physiologically or, more often, in response to mechanical traumas (incisions, cuts) or to a stress (attack by pathogens), comprised of a complex group of solid, translucid, occasionally liquid substances, insoluble in water, soluble in alcohol, acetone, ether and chloroform.

Such resins contain complex mixtures of aliphatic alcohols or acids, lignans, resin acids, resinotannols, esters and resenes (originating from essential oil terpenes polymerizing and oxidising processes), etc.

From a chemical standpoint, many different components are found in resins: aliphatic alcohols or acids of different carbon chain length, free aromatic acids, resin acids, monoterpene alcohols, diterpene alcohols, triterpene alcohols, resinols, phenolic compounds belonging to the sterol family, etc.

The composition could contain said resins in a powdered granulate form, or in the form of a dry extract and/or lyophilised extract and/or fractions of said extracts.

The forms in which these resins or extracts thereof can be used for the preparation of compositions for oral use are known in the literature, and the technician in the field needs no further teachings in that sense.

By way of non-limiting example, in case of preparation of an extract, the resin could be treated with 20%, or 30%, or 40%, or 50%, or 60%, or 70%, or 80% hydroalcoholic solutions; the alcohols could be methanol, ethanol, isopropanol; in a specific embodiment, ethanol will be used. The alcoholic extract obtained will be subjected to filtration, concentration, and drying to provide the corresponding dry extract.

The dry product obtained could be powdered, granulated or anyhow treated for a suitable mixing with the other components.

The resins according to the invention may be resins suitable for preparing compositions for topical use (oral and/or non-oral, such as for compositions for skin use and/or for the rectal mucosa and/or for the vaginal mucosa and/or for the uterine mucosa) commonly used in the pharmaceutical and/or food field.

However, as mentioned hereto, a preferred embodiment envisages the use of resins of plant origin. The technician in the field knows that all officinal plants containing resins or mixtures thereof can be used for this purpose. According to the present invention, resins can be, e.g., represented by incense, myrrh, or mixtures thereof. However, the technician in the field will know how to identify additional resins besides those indicated here by analogy.

In a preferred embodiment, said resins could be extracted in a more or less purified form from *Commiphora myrrha* and/or from *Boswellia* spp.

Examples of *Boswellia* species comprising resins are, e.g., *Boswellia sacra, B. frereana, B. papyrifera* and *B. serrata*.

According to one embodiment of the composition of the invention, said resins could therefore be comprised in *Commiphora myrrha* and/or *Boswellia* spp. extracts as long as the w/w (percentage in weight) concentration of said components complies with the above-indicated concentrations, and therefore sufficient plant extract/s, capable of providing the desired concentration of resins, be present.

The tannins of the composition of the invention can be synthetic or of plant origin (or a mixture thereof) and can be, as already mentioned, hydrolisable tannins, condensed tannins or a mixture thereof.

As to tannins of plant origin, several officinal plants comprising tannins are known to the technician in the field. Tannins, more or less purified, extracted from one or more plant sources of tannins can be used for realizing the invention.

According to a preferred embodiment, said tannins are extracted from one or more of, and/or are comprised in extracts of one or more of *Agrimonia eupatoria, Hamamelis Virginiana, Vaccinium myrtillus, Quercus robur, Potentilla anserina, Rosa centifolia, Helichrysum angustifolium* or other plants rich in tannins or mixtures of two or more of said extracts.

As mentioned above for resins, in one embodiment of the invention, tannins could be comprised in extracts of said plants or mixtures thereof, as long as the w/w (percentage in weight) concentration of said components complies with the above-indicated concentrations, and therefore sufficient plant extract/s, able to provide the desired concentration of tannins, be present.

In one embodiment, resins are comprised in the suitable plant extracts, e.g. of *Commiphora myrrha* and/or from *Boswellia* spp. according to what described above, and also tannins are comprised in plant extracts of one or more from *Agrimonia eupatoria, Hamamelis Virginiana, Vaccinium myrtillus, Quercus robur, Potentilla anserina, Rosa centifolia, Helichrysum angustifolium*, or other plants rich in tannins or mixtures of two or more of said extracts.

The polysaccharides according to the invention are polysaccharides present in natural products, or in plant extracts or obtainable from plants.

In one embodiment, these polysaccharides are of plant origin and are represented by polysaccharide macromolecules that, into contact with water, form colloidal solutions or gels and can also be defined as plant hydrocolloids.

These polysaccharides are normal constituents of the plant cells preserved in predefined histological structures. They are polymers of sugars and are characterised by good stability, non-toxicity, hydrophilic properties and biodegradability.

A non-limiting example of polysaccharides that can be used in the present invention is given by polysaccharides extracted from *Aloe vera*, Camomile, Althea, Plantain and other plants rich in polysaccharides.

In one embodiment, plant extracts comprising polysaccharides, such as (but not limited to) extracts of *Aloe vera*, Camomile, Althea and other plants rich in polysaccharides, could be used directly.

According to an embodiment of the present invention, the composition will comprise extract of *Aloe vera* as a source of polysaccharides.

In one embodiment, said extract is an extract of dehydrated leaf gel or other extracts rich in polysaccharides.

In a specific embodiment of the invention, as parts of the plant, the dehydrated leaf gel will be used for the *aloe*, the whole flowers or ligulates will be used for the camomile, the roots will be used for the althea, and the leaves will be used for the lemon-balm.

In a specific embodiment of the invention the composition comprises
from 0.05 to 1% w/w of resins,
from 0.05 to 1% w/w of tannins, and
from 0.05 to 3% w/w of polysaccharides
wherein said resins of plant origin are extracted from and/or are comprised in extracts of *Commiphora myrrha*, said tannins of plant origin are extracted from and/or are comprised in extracts of *Agrimonia eupatoria*, and said polysaccharides of plant origin are extracted from and/or are comprised in extracts of *Aloe vera*.

In another embodiment, the composition comprises
from 0.1 to 0.7% w/w of resins,
from 0.1 to 0.8% w/w of tannins, and
from 0.1 to 1.5% w/w of polysaccharides,
wherein said resins of plant origin are extracted from and/or are comprised in extracts of *Commiphora myrrha*, said tannins of plant origin are extracted from and/or are comprised in extracts of *Agrimonia eupatoria*, and said polysaccharides of plant origin are extracted from and/or are comprised in extracts of *Aloe vera*.

According to a further embodiment, the composition comprises
from 0.1 to 0.5% w/w of resins,
from 0.2 to 0.7% w/w of tannins, and
from 0.1 to 0.8% w/w of polysaccharides
wherein said resins of plant origin are extracted from and/or are comprised in extracts of *Commiphora myrrha*, said tannins of plant origin are extracted from and/or are comprised in extracts of *Agrimonia eupatoria*, and said polysaccharides of plant origin are extracted from and/or are comprised in extracts of *Aloe vera*.

For all components of the composition of the invention listed above, use in the form of dry extract and/or lyophilised extract and/or fractions of such extracts is suitable. All examples provided herein are non-limiting and are to be understood as possible embodiments of the composition according to the invention.

Given its features, among which the adhesion ability of tannins, which carry out the various therapeutic actions listed in the state of the art and reported again herein, the invention relates in particular to the composition, according to any one of the above-described embodiments, for use in a medical treatment by administration to a subject in need thereof; said subject being a mammal, human being included.

The composition of the invention could be used in the treatment, or as adjuvant in the treatment of pathologies involving the oral mucosa, the gastric mucosa, the enteric mucosa, the rectal mucosa, the vaginal mucosa, the uterine mucosa. For instance, without wishing to limit the invention, the composition could be used for the treatment of enteritis, Crohn's disease, ulcerous colitis, gastritis, esophagitis, mucosal or skin ulcers, pharyngeal cavity inflammations, such as sore throat, cough, burnings, eczemas, viral infections and diseases of the buccal, pharynx, gastric, airway, intestinal, uterine, rectal mucosa.

According to a specific embodiment, the invention can be used in the treatment of sore throat and/or of pharynx inflammations.

The term "pharynx" as used herein comprises nasopharynx, oropharynx and hypopharynx (or laryngopharynx).

The compositions of the invention can be prepared by thoroughly mixing the above-indicated components with a carrier and/or a diluent and/or a pharmaceutical excipient according to techniques for conventional pharmaceutical preparations. The carrier can have a wide variety of forms depending on the desired administration pathway (e.g., oral, topical, rectal). Therefore, for liquid oral preparations, such as suspensions, elixirs and solutions, suitable carriers and additives include water, glycols, oils, alcohols, aromatizers, preservatives, stabilizers, diluents and the like; for solid oral preparations, such as powders, tablets and pills, suitable carriers and additives include starches, sugars, diluents, granulating agents, lubricants, binders (binding agents), disintegrants and the like. Solid oral preparations can also be coated with substances such as sugars, or have enteric coatings to modulate the site of maximum absorption.

By way of example, in the category of diluents there can usefully be employed diluents for solid formulations, such as sugars, polyalcohols (for example, lactose, mannitol, sorbitol), cellulose, salts of inorganic acids (such as, e.g., dibasic calcium phosphate) salts of organic acids (such as citrates, carbonate and bicarbonate tartrates in the form of salts of sodium, potassium and calcium) or diluents for liquid forms such as water, edible oils for oral use (sunflower oil, olive oil, corn oil, sweet almond oil, nut oil) or used for topical formulations (jojoba oil, short-chain, medium-chain or long-chain triglycerides), polyalcohols (glycerin, propylene glycol, hexylene glycol).

In the category of disintegrants, it is possible to use, for example, natural or modified starches (corn starch, rice starch, potato starch) croscaramellose sodium, glycolate sodium starch, crospovidone; possible binders that can be used include natural products of gum type (guar gum, xanthan gum, gum arabic), sucrose and synthesis products, including polyvinyl pyrrolidone and semi-synthetic derivatives of cellulose. As lubricants, stearic salts and salts thereof, such as the salt of magnesium, polymers of ethylene glycol, triglycerides and natural or synthetic waxes are effectively employed.

Surfactants are used to make the active ingredients contained in the formulations forming the basis of the invention more soluble or washable with water, these active ingredients acting alone or carried by one or more diluents. For example, sorbitan esters, sorbitan polyoxyethylene esters, sucrose esters and sodium lauryl sulphate can be cited.

Slip agents may be selected for example from colloidal silica, precipitated silica, whereas anti-adherents that can be used include, for example, talc or starch.

The composition of the invention may be realized as a composition for topical use, such as in the form of cream, pomade, ointment, spray, gel, suppository, ovule, or even for oral use, such as in the form of capsule, tablet, pill, hard gelatine, soft gelatine, granule, powder, syrup, elixir, suspension, emulsion, or as aerosol, and comprises at least one agent selected from a carrier and/or a diluent and/or an excipient that could be selected among excipients or adjuvants technically used in common pharmaceutical or cosmetic practice or in the food industry. The excipients used could belong to the categories of diluents, solubilisers, disgregants, binders, lubricants, surfactants, slip agents and anti-adherents.

In one embodiment, the composition may also contain flavourings, colorants and preservatives commonly used in the pharmaceutical, cosmetic and food industries. Merely by way of example, a formulation in capsules could be prepared conveniently by grinding beforehand the composition of the invention, mixing in a common mixer the powder obtained together with one or more excipients selected to prepare the formulation, such as for example a diluent, a disintegrant, a lubricant and a slip agent selected from those mentioned above or available on the market and approved for oral use.

In the case of a tablet, it could be necessary to granulate some or all of the mixture with a binding agent dissolved beforehand in water or introduced in mixture and using the water as an adjuvant of the process of granulation in accordance with what is known in the prior art.

The granulate could be dried, sieved and further mixed with other powders for the purpose of obtaining a mixture suitable for obtaining tablets in accordance with what is known to a technician in the field.

For oral administration the composition could be made in the form of daily unit dosage or of fractions of daily unit dosage (e.g., 2, 3, 4, 5, 6, or more capsules, tablets, pills, granule or powder single-doses, or gelatins could be taken over the day, according to the judgment of the doctor in charge), and may contain conventional excipients, including, e.g., binding agents, like gum arabic, gelatine, sorbitol, gum tragacanth, and/or polyvinylpyrrolidone; fillers, like lactose, sugar, corn starch, rice starch, calcium phosphate, sorbitol and/or glycine; tableting lubricants, like magnesium stearate, talc, polyethylenglycol and/or silica; disintegrants, e.g. potato starch; and moisturizers like sodium laurylsulphate. The tablets can be coated according to methods well known in the standard pharmaceutical practice.

The composition could also be made in a liquid or semi-liquid form, as a suspension, emulsion, solution for oral administration, and could optionally contain natural aromatizing agents giving a palatable taste thereto.

The composition in the form of powder or granule could be pre-metered in suitable containers and ready for use, either by ingestion as such or to be resuspended in an appropriate liquid such as water, tea, etc. In this case as well, the composition could contain natural aromatizing agents giving a palatable taste thereto.

According to some preferred embodiments, the composition can therefore be, for example, for topical use, in the form of cream, pomade, ointment, spray, gel, suppository, ovule; or for oral use, in the form of capsule, a tablet, a pill, a hard gelatine, a soft gelatine, a granule, a powder, a syrup, an elixir, a suspension, an emulsion, a spray.

in the Examples section, some examples of embodiments of the composition in forms for oral use are provided by way of illustration and not for limitative purposes.

Evidently, all of the above-indicated excipients could be used in a pharmaceutically acceptable grade.

In one embodiment the composition as described herein, in any one of the above-indicated embodiments, could be in the form of pharmaceutical composition, or comprise pharmaceutical grade ingredients, or could consist in or be comprised in a medical food or in a medical device.

The composition according to the present description could be made in the form of pharmaceutical composition or of medical device according to any one of the classes described in Directive 93/42/EEC on medical devices (comprising also substances and not only "devices" in the mechanical sense of the term), or in the form of nutraceutic, of medical food, food supplement, or in any suitable form according to the regulatory provisions of the Country in which said composition will be produced.

The medical device or the medical food could also contain as ingredients other components, comprising, e.g., combinations of vitamins, mineral salts and other substances directed at diet supplementing.

In one embodiment of the invention, the invention will comprise only components of natural origin and/or of plant origin (coming from parts of plants or from substances produced by the plants).

Object of the invention is also a medical treatment wherein the composition of the invention is administered in one or more daily doses to a subject in need thereof; said subject being a mammal, human being included.

According to the invention, the treatment may be a therapeutic treatment wherein the composition of the invention is administered for the treatment or as adjuvant of the treatment of pathologies involving the oral mucosa, the gastric mucosa, the enteric (intestinal) mucosa, the rectal mucosa, the vaginal mucosa, the uterine mucosa. For instance, without wishing to limit the invention, the treatment of the invention could be for the treatment or for assisting in the treatment of enteritis, Crohn's disease, ulcerous colitis, gastritis, esophagitis, mucosal or skin ulcers, inflammations of the pharyngeal cavity, such as sore throat, cough, burnings, eczemas, viral infections and diseases of the buccal, pharynx, gastric, airway, intestinal, uterine, rectal mucosa.

According to a specific embodiment of the invention, said treatment will be a treatment for the treatment or for assisting in the treatment of sore throat and/or of pharynx inflammations.

The term "pharynx" as used herein comprises nasopharynx, oropharynx and hypopharynx (or laringopharynx).

The treatment according to the invention can comprise the administration of the composition of the invention in the form of daily unit dosage or of fractions of daily unit dosage (e.g., 2, 3, 4, 5, 6, or more capsules, tablets, granule or powder single-doses, syrup or fluid or gelatins could be taken over the day, according to the judgment of the doctor in charge), Examples of some embodiments of the composition according to the invention are reported herebelow. Said examples are provided merely by way of a non-limiting illustration thereof.

The technician in the field, starting from the indications provided in the present application, will be able to realize, by applying common techniques of pharmaceutical formulation, the present invention even in forms not expressly exemplified below, but described, such as, e.g., formulations for topical or rectal or vaginal or uterine use.

Composition/Formulation Examples

Composition Example 1

Tablets

Composition Example A*

TABLE 1

| Components | % w/w in the formulation |
|---|---|
| Resins | 0.05-0.7% |
| Tannins | 0.5-1% |
| Polysaccharides | 0.5-1.5% |
| Carriers/excipients/Other | 96.8-98.95% |

Composition Example B*

TABLE 2

| Components | % w/w in the formulation |
|---|---|
| Resins | 0.16-0.48% |
| Tannins | 0.43-0.62% |
| Polysaccharides | 0.34-0.66% |
| Carriers/excipients/Other | 98.24-99.07% |

In both formulation examples there were used: lyophilised myrrh extract as a source of resins, dried aqueous *agrimonia* extract or lyophilised *hamamelis* extract or a mixture thereof as a source of tannins and dry *Aloe vera* extract as a source of polysaccharides.

Formulation Example 1

1500 ma tablets (daily dose: 1-4 tablets)

TABLE 3

| TABLET | % |
|---|---|
| LOOSE CANE SUGAR, P.I. | 89.39 |
| LOOSE LYOPHILISED MYRRH EXTRACT | 0.5-2 |
| DRIED AQUEOUS *AGRIMONIA* EXTRACT | 4-10 |
| DRY *ALOE VERA* EXTRACT 200 | 0.5-3 |
| AROMAS/CARRIERS/EXCIPIENTS | q.s. to 100 |

Natural aromas: balsamic mint, *eucalyptus*; Carriers/Excipients: cane sugar, mint essential oil, *eucalyptus* essential oil.

Composition Example 2

Spray

Composition Example C*

TABLE 4

| Components | % w/w in the formulation |
|---|---|
| Resins | 0.15-0.7% |
| Tannins | 0.05-0.5% |
| Polysaccharides | 0.1-1.5% |
| Carriers/excipients/Other | 97.3-99.7% |

Composition Example D*

TABLE 5

| Components | % w/w in the formulation |
|---|---|
| Resins | 0.15-0.7% |
| Tannins | 0.5-1% |
| Polysaccharides | 0.1-1.5% |
| Carriers/excipients/Other | 96.8-99.25% |

In both formulation examples, there were used: lyophilised myrrh extract as a source of resins, dried aqueous *agrimonia* extract or lyophilised *hamamelis* extract or a mixture thereof as a source of tannins and dry *Aloe vera* extract as a source of polysaccharides.

Formulation Example 2

Nebulization spray, Alcohol grade 22-28; density 1.0-1.2 g/ml; single nebulization 1.5-2 (about 1.7) ml, 12-16 nebulizations/day

TABLE 6

| SPRAY 1 | % |
|---|---|
| MYRRH T.M. | 26-35 |
| LYOPHILISED MYRRH EXTRACT | 0.1-1 |
| DRIED AQUEOUS *AGRIMONIA* EXTRACT | 2-4 |
| DRY *ALOE VERA* EXTRACT | 0.1-1.5 |
| AROMAS/CARRIERS/EXCIPIENTS* | q.s. to 100 |

TABLE 7

| SPRAY 2 | % |
|---|---|
| MYRRH T.M. | 26-35 |
| LYOPHILISED MYRRH EXTRACT | 0.1-1 |
| LYOPHILISED *HAMAMELIS* EXTRACT | 2-4 |
| DRY *ALOE VERA* EXTRACT | 0.1-1.5 |
| AROMAS/CARRIERS/EXCIPIENTS* | q.s. to 100 |

Natural aromas: Lemon and others; Carriers/Excipients: vegetable glycerin, deionized water, xanthan gum, concentrated apple juice, *eucalyptus* essential oil, mint essential oil.

Comparative Examples

1. Assessment of interaction among plant extracts containing tannins, plant extracts not containing tannins and oral mucosa.

2 μm-thick sections of untreated white male mouse oropharynx, fixed in formalin with 10% phosphate buffer, were used.

Separate deparaffinized and hydrated sections were treated for 1 hour, respectively with 1—10%, 5%, 1% and 0.1% tannic acid in distilled water (weight/volume)

2—10%, 5%, 1% and 0.1% *Agrimonia eupatoria* extract in distilled water (w/v), equal to, respectively, 100 mg/ml, 50 mg/ml, 10 mg/ml and 1 mg/ml of *Agrimonia eupatoria*

3—10%, 5%, 1% and 0.1% *Hamamelis Virginiana* extract in distilled water (w/v), equal to, respectively, 100 mg/ml, 50 mg/ml, 10 mg/ml and 1 mg/ml of *Hamamelis Virginiana*

4—10%, 5%, 1% and 0.1% *Aloe vera* extract in distilled water (w/v)

5—10%, 5%, 1% and 0.1% *Commiphora myrrha* in distilled water (w/v)

6—composition of the invention in the form of tablets (composition example B) in a 10%, 20% 30% and 50% solution, equal to, respectively, 6.67 mg/ml, 13.34 mg/ml, 20.01 mg/ml and 33.35 mg/ml of *Agrimonia eupatoria*

7—composition of the invention in the form of spray (composition example C) in a 10%, 20%, 50% and 100% solution, equal to, respectively, 3.3 mg/ml, 6.6 mg/ml, 16.5 mg/ml and 33 mg/ml of *Agrimonia eupatoria*, 8—composition of the invention in the form of spray (composition example D) in a 10%, 20% 50% and 100% solution, equal to, respectively, 3.3 mg/ml, 6.6 mg/ml, 16.5 mg/ml and 33 mg/ml of *Hamamelis Virginiana*.

9-composition of the invention (composition example C) without *Agrimonia eupatoria* in a 10%, 20%, 50% and 100% solution rinsed with distilled water and then stained with 2% FeCl₃ for 15 minutes, again washed with distilled water, alcohol and xylene and then prepared in Enthellane.

The sections were analyzed at the optical microscope (40× magnification) and photographed with a digital camera.

In FIGS. 1, 2, 3, 4 and 5, the staining obtained with the above-described samples 1, 2, 3, 4 and 5, at the concentrations described above, is reported.

Evidently, samples 4 and 5 exhibit substantially no staining.

In FIG. 6, are shown for comparison panel 6*a*: samples 2 and 6 panel 6*b*: samples 2, 7 and 9 panel 6*c*: samples 3 and 8

As is evident from FIG. 6, the presence of resins and of polysaccharides increases in a clearly visible manner the ability of tannins, highlighted by the dye used, to adhere to the oral mucosa.

In panel 6*a* it is distinctly seen how the composition of the invention has the effect of causing a staining, with only 6.7 mg/ml of *agrimonia*, equal to that obtained with an amount of from 50 to 100 mg/ml of *agrimonia*.

Panel A:

(In the experiments, the same *agrimonia* extract was used, both in distilled water (Table 8 below) and in the example of composition A (Table 9 below)

TABLE 8

| Examined solution | *Agrimonia* extract concentration (mg/ml) |
|---|---|
| 0.1% *Agrimonia* | 1 |
| 1% *Agrimonia* | 10 |
| 5% *Agrimonia* | 50 |
| 10% *Agrimonia* | 100 |

TABLE 9

| Composition Example A | *Agrimonia* extract concentration (mg/ml) |
|---|---|
| in 10% distilled water | 6.67 |
| in 20% distilled water | 13.34 |
| in 30% distilled water | 20.01 |
| in 50% distilled water | 33.35 |

(Tannins were titrated as pyrogallol on dried aqueous *agrimonia* extract by standard spectrophotometric method, mean % 7.5±about 2% as variation)

In panel 6*b* it is evident how another embodiment of the composition of the invention, has the effect of causing a staining, with about 6.6 mg/ml of *agrimonia*, equal to that obtained with an amount of from 50 to 100 mg/ml of *agrimonia*, and how said composition without *agrimonia* causes no staining: staining is therefore actually due only to tannins present in the *agrimonia* extract, whereas staining intensity, *agrimonia* extract concentration being equal, is clearly linked to the presence of resins and polysaccharides according to the invention.

Panel B:

In the experiments, the same *agrimonia* extract was used, both in distilled water (Table 10 below) and in the example of composition A (Table 11 below)

TABLE 10

| Examined solution | *Agrimonia* extract concentration (mg/ml) |
|---|---|
| 0.1% *Agrimonia* | 1 |
| 1% *Agrimonia* | 10 |
| 5% *Agrimonia* | 50 |
| 10% *Agrimonia* | 100 |

TABLE 11

| Composition example B | *Agrimonia* extract concentration (mg/ml) |
|---|---|
| 10% | 3.3 |
| 20% | 6.6 |
| 50% | 16.5 |
| 100% | 33 |

(Tannins were titrated as pyrogallol on dried aqueous *agrimonia* extract by standard spectrophotometric method, mean % 7.5±about 2% as variation)

Finally, in panel 6*c*, the effectiveness of the composition of the invention is confirmed in a further embodiment; in this case as well, it is evident how with an amount of composition containing about 6.6 mg/ml of *hamamelis*, a staining equal to that obtained with an amount of from 50 to 100 mg/ml of *hamamelis* is obtained. It is also evident how said composition without *hamamelis* causes no staining: staining is therefore due only to tannins present in the *hamamelis* extract, whereas staining intensity, *hamamelis* extract concentration being equal, is clearly linked to the presence of resins and polysaccharides according to the invention.

Panel B:

(In the experiments, the same *hamamelis* extract was used, both in distilled water (Table 12 below) and in the example of composition C (Table 13 below)

TABLE 12

| Examined solution | *Hamamelis* extract concentration (mg/ml) |
|---|---|
| 0.1% *hamamelis* | 1 |
| 1% *hamamelis* | 10 |
| 5% *hamamelis* | 50 |
| 10% *hamamelis* | 100 |

TABLE 13

| Composition example C | *Hamamelis* extract concentration (mg/ml) |
|---|---|
| 10% Gol. Spray H | 3.3 |
| 20% Gol. Spray H | 6.6 |
| 50% Gol. Spray H | 16.5 |
| 100% Gol. Spray H | 33 |

(Tannins were titrated as pyrogallol on lyophilised *hamamelis* extract by standard spectrophotometric method, mean % 26±about 4% as variation)

As is evident from the figures, the data therefore demonstrate the effect of the composition of the invention in increasing, of about a factor 10, tannins' binding effectiveness to the oral mucosa.

The invention claimed is:

1. A composition comprising by weight percent thereof: from 0.05 to 1% w/w of resins, from 0.05 to 1% w/w of tannins, and
from 0.05 to 3% w/w of polysaccharides,
wherein the composition is in the form suitable for treating a mucosal or skin tissue, and wherein the amounts of said resins, tannins, and polysaccharides are therapeutically effective amounts sufficient to provide increased mucosal or skin adhesion versus a reference tannin composition lacking said amounts of resins and/or polysaccharides.

2. The composition according to claim 1, comprising
from 0.1 to 0.7% w/w of resins,
from 0.1 to 0.8% w/w of tannins, and
from 0.1 to 1.5% w/w of polysaccharides.

3. The composition according to claim 1, comprising
from 0.1 to 0.5% w/w of resins,
from 0.2 to 0.7% w/w of tannins, and
from 0.1 to 0.8% w/w of polysaccharides.

4. The composition according to claim 1, wherein said resins and/or wherein said tannins and/or wherein said polysaccharides are of natural origin.

5. The composition according to claim 1, wherein said tannins are hydrolisable tannins and/or condensed tannins.

6. The composition according to claim 1, wherein said resins are extracted from and/or are comprised in extracts of *Commiphora myrrha* and/or of *Boswellia* spp.

7. The composition according to claim 1, wherein said tannins are extracted from and/or are comprised in extracts of one or more selected from the group consisting of *Agrimonia eupatoria, Hamamelis Virginiana, Vaccinium myrtillus, Quercus robur, Potentilla anserina*, and *Rosa centifolia*.

8. The composition according to claim 1, wherein said polysaccharides are extracted from and/or are comprised in extracts of one or more selected from the group consisting of *Aloe vera, Matricaria chamomilla*, and *Althaea officinalis*.

9. The composition according to claim 1, further comprising at least one edible and/or pharmaceutically acceptable carrier and/or diluent and/or excipient.

10. The composition according to claim 1, which is for topical use in the form of cream, pomade, ointment, spray, gel, suppository, or ovule; or for oral use in the form of a capsule, a tablet, a pill, a hard gelatine, a soft gelatine, a granule, a powder, a syrup, an elixir, a suspension, an emulsion, a spray, or in the form of aerosol.

11. The composition according to claim 1, which is a pharmaceutical composition, is comprised in or consists in a food supplement, is comprised in or consists in a medical device, is comprised in or consists in a medical food, or is comprised in or consists in a nutraceutical.

12. A nutraceutical medical device, food supplement, or medical food comprising a composition according to claim 1.

13. A method of using a composition according to claim 1 for medical treatment, wherein said method comprises administering a therapeutically effective amount of said composition to a subject in need thereof.

14. The method according to claim 13, for treatment of mucosal inflammation, skin inflammation, mucosal or skin ulcer, mucosal or skin wound, or burning.

15. The method according to claim 14, for treatment of enteritis, Crohn's disease, ulcerous colitis, gastritis, esophagitis, mucosal or skin ulcer, pharynx inflammation, sore throat, cough, burning, eczema, viral infection, or a disease of buccal, pharynx, gastric, airway, intestinal, uterine, or rectal mucosa.

16. The method according to claim 13, wherein said composition further comprises at least one edible and/or pharmaceutically acceptable carrier and/or diluent and/or excipient.

17. The method according to claim 13, wherein said composition is for topical use in the form of cream, pomade, ointment, spray, gel, suppository, ovule; or for oral use in the form of a capsule, a tablet, a pill, a hard gelatine, a soft gelatine, a granule, a powder, a syrup, an elixir, a suspension, an emulsion, a spray, or in the form of aerosol.

18. The method according to claim 13, wherein said composition is a pharmaceutical composition, is comprised in or consists in a food supplement, is comprised in or consists in a medical device, is comprised in or consists in a medical food, or comprised in or consists in a nutraceutical.

* * * * *